US010016751B2

(12) United States Patent
Monnier et al.

(10) Patent No.: US 10,016,751 B2
(45) Date of Patent: Jul. 10, 2018

(54) SUPPORTED, BIMETALLIC NANOPARTICLES FOR SELECTIVE CATALYSIS

(71) Applicant: University of South Carolina, Columbia, SC (US)

(72) Inventors: John Monnier, Columbia, SC (US); John Regalbuto, Columbia, SC (US); Kerry O'Connell, Columbia, SC (US)

(73) Assignee: University of South Carolina, Columbia, SC (US)

(*) Notice: Subject to any disclaimer, the term of this patent is extended or adjusted under 35 U.S.C. 154(b) by 228 days.

(21) Appl. No.: 14/854,191

(22) Filed: Sep. 15, 2015

(65) Prior Publication Data

US 2016/0136632 A1   May 19, 2016

Related U.S. Application Data

(60) Provisional application No. 62/050,428, filed on Sep. 15, 2014.

(51) Int. Cl.
| | |
|---|---|
| *B01J 35/02* | (2006.01) |
| *B01J 23/52* | (2006.01) |
| *C01B 3/40* | (2006.01) |
| *B01J 23/42* | (2006.01) |
| *B01J 23/40* | (2006.01) |

(Continued)

(52) U.S. Cl.
CPC ............ *B01J 35/026* (2013.01); *B01J 23/40* (2013.01); *B01J 23/42* (2013.01); *B01J 23/52* (2013.01); *C01B 3/40* (2013.01); *C01B 17/502* (2013.01); *C07C 17/08* (2013.01); *C01B 2203/0238* (2013.01); *C01B 2203/107* (2013.01); *C01B 2203/1047* (2013.01); *C01B 2203/1058* (2013.01); *C01B 2203/1064* (2013.01); *C01B 2203/1082* (2013.01);
(Continued)

(58) Field of Classification Search
CPC .................................. B01J 21/18; B01J 23/52
See application file for complete search history.

(56) References Cited

U.S. PATENT DOCUMENTS

| | | | | |
|---|---|---|---|---|
| 2009/0130518 A1* | 5/2009 | Lee | ........................ | H01M 4/885 |
| | | | | 429/532 |
| 2011/0086295 A1* | 4/2011 | Lopez | ................... | H01M 4/921 |
| | | | | 429/524 |

(Continued)

OTHER PUBLICATIONS

C.H. Bartholomew and R.J. Farrauto, "Fundamentals of Industrial Catalytic Processes," John Wiley and Sons, Hoboken, NJ, 2006, pp. 274-286.

(Continued)

*Primary Examiner* — Jun Li
(74) *Attorney, Agent, or Firm* — Dority & Manning, P.A.

(57) ABSTRACT

Supported, bimetallic catalyst systems are provided. The supported, bimetallic catalyst system can include a support defining a surface; a core metal positioned on the surface of the support; and a shell metal positioned on the core metal to form a core-shell particle on the surface of the support. The core metal has a surface free energy that is higher than a surface free energy of the shell metal. Methods are also provided for the formation of such supported, bimetallic catalyst systems, as well as the use of such supported, bimetallic catalyst systems in chemical processes.

16 Claims, 1 Drawing Sheet

(51) Int. Cl.
C01B 17/50 (2006.01)
C07C 17/08 (2006.01)
(52) U.S. Cl.
CPC ..... C01B 2203/1241 (2013.01); Y02P 20/142 (2015.11); Y02P 20/52 (2015.11)

(56) References Cited

U.S. PATENT DOCUMENTS

| | | | | |
|---|---|---|---|---|
| 2011/0143934 A1* | 6/2011 | Shao | ........................ | B01J 23/42 502/313 |
| 2011/0183128 A1* | 7/2011 | Magdassi | ................ | B01J 13/02 428/207 |
| 2011/0275009 A1* | 11/2011 | Goto | ........................ | B01J 23/42 429/506 |
| 2012/0046164 A1* | 2/2012 | Tanaka | .................... | B01J 21/18 502/319 |
| 2013/0022899 A1* | 1/2013 | Arai | ........................ | C23C 18/31 429/524 |
| 2013/0059231 A1* | 3/2013 | Hwang | ................ | H01M 4/921 429/524 |
| 2015/0333336 A1* | 11/2015 | Cho | ........................ | B01J 37/16 429/524 |

OTHER PUBLICATIONS

S.N. Rashkeev, D.M. Ginosar, L.M. Petkovic, and H.H. Farrell, "Catalytic activity of suppported metal Particles for sulfuric acid decompositionreaction," Catal. Today, 139 (2009) 291.
H. Er-Rbib, C. Bouallou, and C. Werkoff, "Production of synthetic gasoline and diesel fuel from dry reforming of methane," Energy Procedia, 29 (2012) 156.
B.P. Navarro, M.C. Alvaraz-Galvan, R. Guil-Lopez, S. Al-Sayari, and J.L.G. Fierro, "Renewable syngas production via dry reforming of methane by CO2: a valuable source of carbon," Green Energy and Technol. (2013) 45.
D.R. O'Keefe, J.H. Norman, and D.G. Williamson, "Catalysis research in thermochemical water-splitting processes, " Catal. Rev.-Sci. Eng., 22 (1980) 325.
J. Zhang, N. Liu, W. Li, B. Dai "Progress on cleaner production of vinyl chloride monomers over non-mercury catalysts," Front. Chem. Sci. Eng. 5 (2011) 514-520.
M. Conte, C.J. Davies, D.J. Morgan, T.E. Davies, A.F. Carley, P. Johnston and G.J. Hutchings, "Modifications of the metal and support during the deactivation and regeneration of Au/C Catalysts for the hydrochlorination of acetylene," Cat. Sci. Technol., 3 (2013) 128.
W. Wittanadecha, N. Laosiripojana, A. Ketcong, N. Ningnuek, P. Praserthdam, J.R Monnier, and S. Assabumrungrat, "Preparation of Au/C catalysts using microwave-assisted and ultrasonic-assisted methods for acetylene hydrochlorination," Appl. Catal A: General, 475 (2014) 292.
G. Ertl, H. Knozinger, J. Weitkamp (Eds.), Handbook of Heterogeneous Catalysis, VCH Verlagsgesellschaft, Weinheim, 1997, pp. 191-386.
Abstract of J.R. Regalbuto, in "Synthesis of Solid Catalysts, Chapter 3: Electrostatic Adsorption," K.de Jong, ed., Wiley-VCH Verlag, 2009.
X. Hao, S. Barnes, and J.R. Regalbuto, "A fundamental study of Pt adsorption onto carbon 1. Adsorption equilibrium and particle synthesis," J. Catal., 279 (2011) 48.
Abstract of S.S. Dkokić, "Electroless deposition of metals and alloys," Mod. Aspects Electrochem., 35, (2002) 51.
M.T. Schaal, A.C. Pickerell, C.T. Williams, and J.R. Monnier, "Characterization and evaluation of Ag—Pt/SiO2 catalysts prepared by electroless deposition," J. Catal., 254 (2008) 131.
K.D. Beard, D. Borelli, A.M. Cramer, D. Blom, J.W. Van Zee, and J.R. Monnier, "Preparation and structural analysis of carbon-supported Co core/Pt shell electrocatalysts using electroless deposition methods," ACS Nano, 3 (2009) 2841.
Rebelli, A.A. Rodriguez, S. Ma, C.T. Williams, J.R. Monnier, "Preparation and characterization of silica-supported, Group IB-Pd bimetallic catalysts prepared by electroless deposition methods," Catal. Today, 160 (2011) 170.
S.H. Overbury, P.A. Bertrand, and G.A. Somorjai, "The surface composition of binary systems. Prediction of surface phase diagrams of solid solutions," Chem. Rev., 75 (1975) 547.
L.Z. Mezey and J. Giber, "The surface free energies of solid chemical elements: calculations from internal free enthalpies of atomization," Jap. J. Appl, Phys., 21 (1982) 1569.
Z. Luo, C.J. Grover, A.C. Reber, S.N. Khanna, and A.W. Castleman, "Probing the magic numbers of alumina-magnesium cluster anions and their reactivity toward oxygen," J. Am. Chem. Soc., 135 (2013) 4307.
P.J. Roach, W.H. Woodward, A.C. Reber, S.N. Khanna, and A.W. Castleman, "Crystal field effects on the reactivity of aluminum-copper cluster anions," Phys. Rev. B, 81 (2010) 195404.
Abstract of P.J. Roach, W.H. Woodward, A.W. Castleman, A.C. Reber, and S.N. Khanna, "Complementary active sites cause size-selectivity of aluminum cluster anions with water," Science, 323 (2009) 492.
A. C. Reber, S. N. Khanna, E. C. Tyo, C. L. Harmon, and A. W. Castleman, Jr., "Cooperative effects in the oxidation of CO by palladium oxide cations", J. Chem. Phys. 135 (2011) 234303.
A. C. Reber and S. N. Khanna, "Effect of N- and P-Type Doping on the Oxygen-Binding Energy and Oxygen Spillover of Supported Palladium Clusters", J. Phys. Chem., 118 (2014) 20306.

* cited by examiner

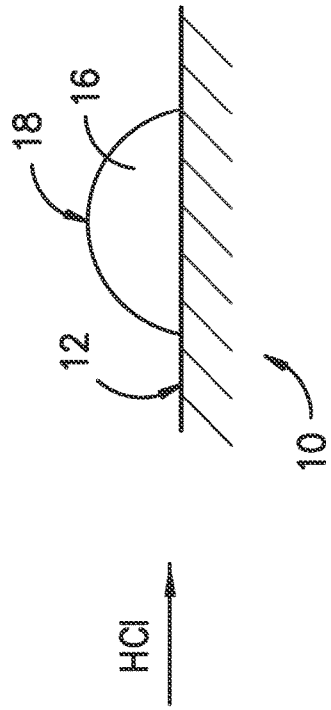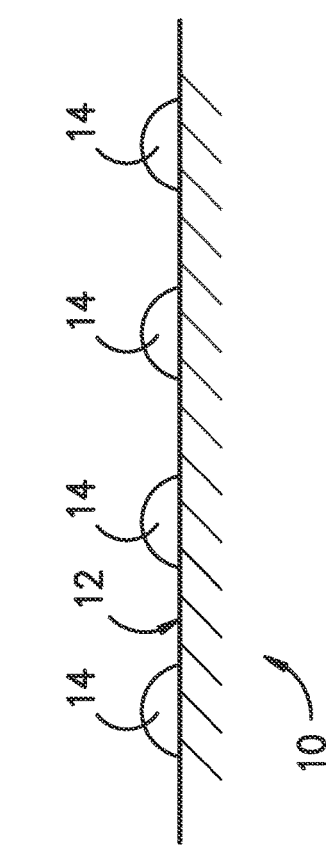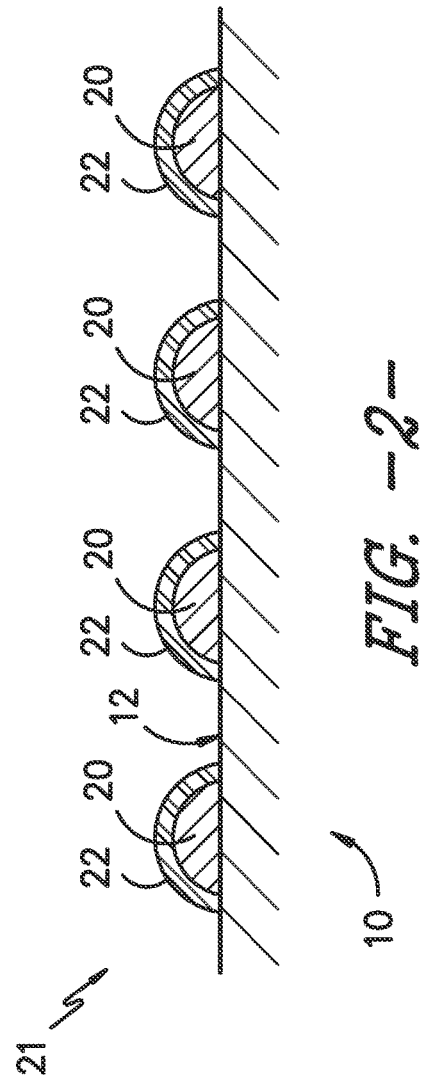

SUPPORTED, BIMETALLIC NANOPARTICLES FOR SELECTIVE CATALYSIS

PRIORITY INFORMATION

The present application claims priority to U.S. Provisional Patent Application Ser. No. 62/050,428 titled "Supported, Bimetallic Nanoparticles for Selective" of Monneir, et al. filed on Sep. 15, 2014, the disclosure of which is incorporated by reference herein.

BACKGROUND

Polyvinyl chloride (PVC) is the third highest volume plastic after polyethylene and polypropylene; global demand is expected to reach 80 billion pounds by 2016. Polyvinyl chloride is produced by polymerization of the vinyl chloride monomer (VCM) which is manufactured either by the oxidative chlorination of ethylene to produce 1,2-dichloroethane which is thermally cracked to produce VCM or by the direct hydrochlorination of acetylene to produce VCM in very high selectivity in a single step. The oxychlorination method generates the majority of VCM, although this route is multi-step, non-selective, and energy intensive. Production of VCM from direct hydrochlorination of acetylene is simple and very selective (>99%), although $HgCl_2$/C, the catalyst currently used, undergoes reduction to Hg metal after a short period of time and is volatilized into the environment. In areas such as China where coal is plentiful, the formation of acetylene from coke ($CaC_2+H_2O$ reaction) is well-developed technology. Thus, it is necessary to develop more environmentally-friendly catalysts for acetylene hydrochlorination.

Carbon-supported Au catalysts have been found to be active and selective catalysts for this reaction. Recent results from our laboratory have shown that, regardless of hydrogen chloride (HCl) pretreatment conditions, all Au/C catalysts exhibit the same activities after 2-3 h of reaction time, indicating that all Au particle sizes and surface compositions are similar. Sintering of Au particles from an initial value of 2 nanometers to a final value of 20 nanometers lowers the exposed surface area of Au by 90%, leading to a concomitant loss of catalytic activity. More recent work has also shown that sintering of Au is directly linked to exposure to HCl, which is, of course one of the essential reactants. If Au can be maintained in the active $AuCl_x$ state during reaction and sintering can be prevented, direct hydrochlorination becomes commercially feasible.

Supported Au catalysts show high activity and selectivity for hydrochlorination of acetylene to vinyl chloride formation. Unfortunately, in the presence of HCl (one of the two reactants), Au particles undergo rapid agglomeration from approximately 2 nm in diameter to form Au particles>20 nm in diameter. FIGS. 1A and 1B depict this agglomeration. As shown in FIG. 1A, the support 10 includes a plurality of Au nanoparticles 14 (e.g., with a diameter of about 2 nm) on its surface 12. Upon exposure to HCl, the Au particles agglomerate into a larger particle 16 (e.g., with a diameter greater than 20 nm) that defines a surface 18 of $AuCl_x$, as shown in FIG. 1B. This loss of Au surface sites greatly limits catalytic activity, making this catalyst and process much less attractive.

SUMMARY

Objects and advantages of the invention will be set forth in part in the following description, or may be obvious from the description, or may be learned through practice of the invention.

Supported, bimetallic catalyst systems are generally provided. In one embodiment, the supported, bimetallic catalyst system includes a support defining a surface; a core metal positioned on the surface of the support; and a shell metal positioned on the core metal to form a core-shell particle on the surface of the support. The core metal has a surface free energy (i.e., a first surface free energy) that is higher than a surface free energy of the shell metal (i.e., a second first surface free energy). Methods are also provided for the formation of such supported, bimetallic catalyst systems.

Methods are also generally provided for the hydrochlorination of acetylene. In one embodiment, the method of hydrochlorination of acetylene includes exposing acetylene to HCl and to a supported, bimetallic catalyst system, such as described above.

Methods are also generally provided for the reduction of sulfur trioxide. In one embodiment, the method of reduction of sulfur trioxide includes exposing sulfur trioxide to a supported, bimetallic catalyst system, such as described above.

Methods are also generally provided form reforming a biogas (e.g., containing methane and carbon dioxide). In one embodiment, the method of reforming a biogas includes exposing the biogas to a supported, bimetallic catalyst system, such as described above, such that a catalytic conversion is achieved to produce hydrogen gas and carbon monoxide.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which:

FIGS. 1A and 1B show a schematic of the agglomeration of Au in the presence of HCl according to the Background discussion (see above); and FIG. 2 shows a schematic of an exemplary bimetallic catalyst system according to one embodiment of the present invention.

Table 1 shows the surface free energy of several materials discussed herein.

Repeat use of reference characters in the present specification and drawings is intended to represent the same or analogous features or elements of the present invention.

Definitions

Chemical elements are discussed in the present disclosure using their common chemical abbreviation, such as commonly found on a periodic table of elements. For example, hydrogen is represented by its common chemical abbreviation H; helium is represented by its common chemical abbreviation He; and so forth.

As used herein, the prefix "nano" refers to the nanometer scale up to about 100 nm. For example, particles having an average diameter on the nanometer scale (e.g., from about 0.1 nm to about 100 nm) are referred to as "nanoparticles."

As used herein, the term "surface free energy" sometimes referred to as "surface energy" or "interface energy" or "surface tension" quantifies the disruption of intermolecular bonds that occur when a surface is created. In the physics of solids, surfaces must be intrinsically less energetically favorable than the bulk of a material (the molecules on the surface have more energy compared with the molecules in the bulk of the material), otherwise there would be a driving force for surfaces to be created to displace the bulk of the material; as a corollary, it is thermodynamically favorable to achieve the lowest possible surface free energy for a surface. Thus, surface free energy may be defined as the excess energy at the surface of a material compared to the bulk. Table 1 above shows the surface free energy of several materials discussed below. Unless otherwise specified, the surface free energy given is in ergs/cm$^2$ at 25° C.

TABLE 1

| Component | Surface free energy (ergs/cm$^2$ surface) |
|---|---|
| Carbon | 506 |
| Au | 1626 |
| Cu | 1934 |
| Pd | 2043 |
| Ni | 2364 |
| Pt | 2691 |
| Co | 2709 |
| Rh | 2828 |
| Mo | 2877 |
| Fe | 2939 |
| Nb | 2983 |
| Re | 3109 |
| Ir | 3231 |
| Ru | 3409 |
| W | 3468 |

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

A bimetallic catalyst system is generally provided, along with methods of its formation and use. In one embodiment, the bimetallic catalyst system includes a support defining a surface, a core metal positioned on the surface of the support, and a shell metal positioned on the core metal to form a core-shell particle on the surface of the support. Importantly, the core metal has a surface free energy that is higher than the surface free energy of the shell metal. As such, the shell metal remains resistant to agglomeration on the surface of the support, and instead remains positioned on the core metal. Thus, the catalyst system maintains its high catalytic activity and makes this process much more economically attractive.

Metal-metal interactions of bimetallic core-shell particles can provide a superior method to maintain catalytic surfaces from sintering. Metal-metal interactions can give greater resistance to particle sintering at conditions typically used for catalytic reactions by using metals with higher surface free energies (SFE) as core materials upon which the shell metal is selectively placed. Surface thermodynamics state that at equilibrium a system composed of solid components will rearrange to the lowest surface free energy; thus, the shell metal with lower SFE will remain on the surface of the core metal having higher SFE. In this manner, the SFE of the bimetallic particle will be thermodynamically most stable.

Referring to FIG. 2, a bimetallic catalyst system 21 is shown including a support 10 defining a surface 12. The bimetallic catalyst is shown on the surface 12 in the form of a core metal 20 and a shell metal 22. As shown, the shell metal 22 completely surrounds the core metal 20, but can be intermittently or partially covering the core in certain embodiments.

In particular embodiments, the core metal 20 defines an average diameter on the surface of the support that is up to about 15 nm (e.g., about 0.5 nm to about 10 nm, such as about 1 nm to about 10 nm). In such embodiments, the shell metal 22 can define a thickness on the core metal that is up to about 20 nm (e.g., about 0.3 nm to about 20 nm, such as about 0.5 nm to about 10 nm, or more particularly about 0.5 nm to about 5 nm). Thus, the shell metal 22 can be a single layer of atoms (i.e., about 0.3 nm for a shell metal of gold) on the core metal up to about 60 layers of atoms (i.e., about 20 nm for a shell metal of gold). The resulting core-shell particle can, in such embodiments, have a total diameter of about 1 nm to about 25 nm on the surface of the support (e.g, about 2 nm to about 15 nm, such as about 2 nm to about 10 nm).

The core-shell particles can cover the surface 12 of the support 10 such that at least about 80% of the surface are of the surface 12 is covered, more preferably about 1 to 50% of the surface is covered, or most preferably about 2 to 30% of the surface is covered. Generally, the support 10 is a solid material having relatively high surface area, the surface of which the bimetallic catalyst system is attached. In most embodiments, the support is inert with respect to the reaction; though the support may participate in the catalytic reaction in certain embodiments. The support 10 generally comprises a material that has a surface free energy that is less than the surface free energy of the core metal 20 and/or the shell metal 22.

Typical supports can include, but are not limited to, various kinds of carbon and/or a metal oxide (e.g., alumina, silica, titania, zirconia, silica-alumina, niobia or mixtures thereof. In one embodiment, the support includes carbon. The carbon support can exist as graphite, carbide, graphene, carbon nanotubes. Other supports can be composed of materials different from metal oxides or carbon. Such supports include silicon carbide, boron nitride, and other metal nitrides.

The core metal 20 generally has a surface free energy that is higher than the surface free energy of the shell metal 22. Depending on the shell metal 22, the core metal 20 can including, but is not limited to, Cu, Pd, Ni, Pt, Co, Rh, Mo, Fe, Nb, Re, Ir, Ru, W, or mixtures thereof.

The metal core can be deposited on the surface of the support using traditional methods such as wet impregnation, incipient wetness, deposition-precipitation, reduction deposition, ion exchange, strong electrostatic adsorption, and combinations of the same. The shell metal 22 can be deposited onto the core metal 20, in one embodiment, utilizing electroless deposition (ED). Electroless deposition is the catalytic or autocatalytic process for deposition of metals by a pre-existing metal (catalysis) or the metal which is being deposited (auto-catalysis). In this catalytic or auto-catalytic process, a chemical reducing agent reduces a water-soluble metallic salt onto specific sites of a pre-existing catalytic surface. This targeted deposition results in the formation of only bimetallic catalysts, and not the wide range of compositions associated with above-mentioned, traditional methods of catalyst preparation. Parameters of electroless deposition include the organic reducing agent (formaldehyde, sodium borohydride, amine boranes, hydrazine, sodium hypophosphite, formic acid, etc.), the reducible metal salt in solution, and/or the pre-existing catalytic core metal surface. By selection of the appropriate deposition parameters, the deposited metal can form a controlled and variable-thickness shell on the surface of the pre-selected core metal. The shell metal 22 can be any suitable catalytic metal, such as gold, platinum, palladium, rhodium, nickel, ruthenium, cobalt, silver, copper or mixtures thereof. As stated, the shell metal 22 has a surface free energy that is lower than the surface free energy of the core metal 20. During the reaction process, the shell metal can remain resistant to agglomeration by remaining on the metal core instead of migrating and agglomerating due to the relative surface free energies of the core metal and the shell metal. The supported, bimetallic catalyst system will tend to keep its surface free energy as low as possible, which means that the shell metal (having a lower surface free energy) will stay on the core metal (having a higher surface free energy). As such, the high catalytic activity of the shell metal can be maintained, making this process much more economically attractive.

Particular supported, bimetallic catalyst systems are disclosed below.

I. Methods of Hydrochlorination of Acetylene

In one embodiment, the supported, bimetallic catalyst system can be utilized in a method for the hydrochlorination of acetylene to form vinyl chloride monomer, which can then be polymerized into PVC. The method can include exposing acetylene to HCl (or another Cl$^-$ ion source) and to a supported, bimetallic catalyst system that has a shell metal that includes gold (Au). In such a supported, bimetallic catalyst system, the core metal has a surface free energy that is higher than the surface free energy of the gold.

Generally, the Au can be deposited as a controlled-thickness layer on top of a suitable core metal (with surface free energy higher than that of Au) such that the Au shell remains resistant to agglomeration and will tend to remain on the metal core. Such a bimetallic catalyst system maintains the high catalytic activity for hydrochlorination and make this process much more economically attractive. $AuCl_x$ forms on the shell metal during the reaction to facilitate formation of the vinyl chloride monomer. In an exemplary reaction, HCl can be present in a molar ratio to acetylene that is greater than 1:1.

In such methods, the extent of conversion of acetylene to vinyl chloride monomer can be maintained at 99% or greater for a significant amount of time, including up to several years of continuous operation, with a continuous supply of Cl$^-$ ions and acetylene feed. The reaction products of this method include the vinyl chloride monomer and smaller amounts of dichloride by-products such as 1,2-dichloroethane and 1,1-dichloroethane.

Table 1 lists surface free energy values at 25° C. for a carbon support (as an exemplary support material), and different metals which can be used as core components for enhanced stabilities of Au shells. The current carbon-supported Au catalyst system, in the absence of HCl, is largely resistant to sintering since the carbon support has lower surface free energy (506 ergs/cm$^2$) than Au, meaning the Au-carbon system is at lowest free energy when the carbon surface constitutes the largest fraction of the total surface. This is the case for smallest Au particles. Obviously, the reaction of HCl with the Au surface must reduce the surface free energy of the chlorided Au species to be on the order of 500 ergs/cm$^2$ since sintering occurs rapidly.

If the Au component exists as a shell on a core of any of the metals shown in Table 1, Au will tend to remain on the higher SFE metal to lower the overall SFE of the system, since migration of Au from the core metal to the carbon support would increase the SFE of the shell-core-support system. For example, the core metal can include Cu, Pd, Ni, Pt, Co, Rh, Mo, Fe, Nb, Re, Ir, Ru, W, or mixtures thereof. Particularly suitable core metals can include Pd, Pt, Ru, Co, or a mixture thereof. The present inventors have found in recent experiments that Pt particles supported on the same carbon support do not undergo sintering when exposed to an HCl gas stream at the same conditions as those where Au undergoes rapid sintering.

That is, in embodiments where Au is deposited as a controlled-thickness layer on a Pt surface, the Au should remain on the Pt surface, since migration of the Au onto the carbon surface would expose the Pt surface which has a much higher SFE (2691 ergs/cm$^2$) than carbon. In fact, use of any of the metals in Table 1 above as a core component can provide a core-shell structure that will resist sintering, since all the core metals have higher SFE values than Au.

In one particular embodiment, a method of electroless deposition can be utilized to selectively deposit Au only on the top of a pre-selected core metal to form the desired core-metal structure. The electroless deposition process involves exposure of a supported, monometallic core metal catalyst (e.g., carbon-supported Pt or Pd) to an aqueous solution containing a suitable reducing agent (e.g., hydrazine ($N_2H_4$), dimethylamine borane (DMAB), or sodium hypophosphite ($NaH_2PO_2$)) and a reducible metal Au salt (e.g., tetrachloroauric acid ($HAuCl_4$) or potassium dicyanoaurate [$KAu(CN)_2$]). Catalytic activation of the reducing agent on the surface of the core metal forms an active reducing species where the Au salt is reduced to form Au metal deposited on the surface of the core metal. Repeated cycles of activation of reducing agent followed by reduction of the Au salt increases the coverage of Au metal on the surface of the core metal. Because the freshly-deposited Au metal is also catalytic for activation of the reducing agent, deposition of Au on the Au surface can also occur after some time interval of this process to form controlled, multi-layers of Au on the core metal surface. The conditions used for electroless deposition include (1) temperatures ranging from about 0° C. to about 150° C., more typically about 10° C. to about 100° C., and most commonly about 20° C. to about 90° C., (2) pH values of the aqueous electroless development bath ranging from about 2 to about 12, and (3) time intervals for completion of the ED process ranging from about 10 minutes to about 140 minutes.

The concentrations of reducible metal salt and reducing agent can be varied to suit the desired coverage of the reducible metal salt, such as $HAuCl_4$ or $KAu(CN)_2$, in this exemplary case. Typically, a molar excess of reducing agent to the reducible metal salt is used to ensure complete reduction of the metal salt. Molar ratios of [reducing agent]/[reducible metal salt] can range from about 2 to about 10 are used for electroless deposition.

In addition to potentially providing a sinter-resistant catalyst with a Au surface, the use of expensive Au can be minimized by using a cheaper core metal such as Cu, Ni, Co, Ru, or even Re with only a thin shell of Au atop the core metal. Even Pt or Pd is cheaper if the resulting Au surface is stable and provides long life for selective hydrochlorination of acetylene. It is believed that this approach of stabilization of supported, core-shell bimetallic nanoparticles using high free energy cores for the formation of high-stability Au catalysts effective for the selective hydrochlorination of acetylene is a novel and very high impact invention.

Although discussed above with respect to the hydrochlorination of acetylene, gold-shell supported, bimetallic catalyst systems can be utilized in any gold catalyzed chemical reactions, particularly those where gold is not consumed by the reaction.

II. Methods of Reduction of $SO_3$ to $SO_2$

In one embodiment, the supported, bimetallic catalyst system can be utilized in a method for the reduction of sulfur trioxide ($SO_3$) to form sulfur dioxide ($SO_2$), which is an essential step in the high temperature, thermochemical splitting of water to form $H_2$ and $O_2$. This is the only completely renewable and environmentally clean method to generate $H_2$ for use as an alternative fuel. Currently, supported Pt catalysts at high temperatures of 600-900° C. are used to catalyze the reduction of $SO_3 \rightarrow SO_2 + \frac{1}{2}O_2$. The active Pt catalyst undergoes rapid sintering at these temperatures and catalyst activity declines rapidly, making this process economically unattractive. The method taught in this Invention Disclosure can include exposing sulfur trioxide to a supported, bimetallic catalyst system that has a shell metal that includes platinum (Pt). In such a supported, bimetallic catalyst system, the core metal has a surface free energy that is higher than the surface free energy of the platinum to avoid sintering of the catalyst in the reaction process. For example, the core metal can be Co, Rh, Mo, Fe, Nb, Re, Ir, Ru, W, or mixtures thereof.

III. Methods of Dry Reforming of Methane (DRM)

In another embodiment the supported, bimetallic catalyst system can be utilized in a process of dry reforming of biogas, which contains large quantities of methane ($CH_4$) and carbon dioxide ($CO_2$). DRM is the catalytic conversion of $CH_4$ and $CO_2$ to synthesis gas (CO and $H_2$) which can efficiently be converted to fuels such as methanol or Fischer-Tropsch liquids. These liquids can be easily stored and sold as higher value products or consumed to produce power at times of peak demand. Since the DRM process is endothermic and requires a heat energy of 261 kJ/mole, a suitable catalyst is required for the reaction to proceed at high temperatures. The major obstacles for current catalysts are carbon deposition, particle sintering, and sulfur poisoning.

Catalysts well known to facilitate the reaction are oxide-supported nickel and platinum group metals (PGMs), such as Pt, Pd, Rh, or mixtures thereof; however, both types of metals have significant limitations. Nickel deactivates rapidly due to carbon and coke formation during the DRM reaction. Further, nickel is severely poisoned by the presence of sulfur, a component present in biogas. PGMs do not have these limitations and are very effective for the DRM reaction; however, PGMs are extremely expensive (orders of magnitude higher than nickel) and undergo sintering at the temperatures for this reaction to proceed efficiently. Electroless deposition can deposit layers, as thin as one atomic monolayer, of expensive PGM metals such as Pt and Pd on inexpensive base metal cores to improve resistance to sintering and lower overall cost of the catalyst, due to the lower cost of the base metal and the thin shell of the PGM component. The only requirement is that the SFE of the core metal be higher than that of the shell metal. Combinations such as Ni cores and Pd shells or Fe cores (SFE=2939 ergs/cm$^2$) and Pt shells are particularly suitable for this reaction. However, the only criterion is that the PGM shell component have a lower SFE than the less expensive core metal.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole and in part. Furthermore, those of ordinary skill in the art will appreciate that the foregoing description is by way of example only, and is not intended to limit the invention so further described in the appended claims.

What is claimed:

1. A supported, bimetallic catalyst system, comprising:
a support defining a surface;
a core metal positioned on the surface of the support, wherein the core metal is platinum; and
a shell metal positioned on the core metal to form a core-shell particle on the surface of the support, wherein the shell metal is gold, and the core metal has a first surface free energy that is higher than a second surface free energy of the shell metal,
wherein the core-shell particles cover at least 80% of the surface of the support.

2. The supported, bimetallic catalyst system as in claim 1, wherein the support comprises a material that has a surface free energy that is less than the surface free energy of the core metal.

3. The supported, bimetallic catalyst system as in claim 1, wherein the support comprises carbon.

4. The supported, bimetallic catalyst system as in claim 3, wherein the support comprises one or more of amorphous carbon, graphite, carbide, and nanotubes.

5. The supported, bimetallic catalyst system as in claim 1, wherein the support comprises a metal oxide.

6. The supported, bimetallic catalyst system as in claim 5, wherein the support comprises alumina, silica, titania, zirconia, silica-alumina, niobia, or mixtures thereof.

7. The supported, bimetallic catalyst system as in claim 1, wherein the core metal defines an average diameter on the surface of the support that is from about 10 nm to about 15 nm.

8. The supported, bimetallic catalyst system as in claim 1, wherein the core metal defines an average diameter on the surface of the support that is about 0.5 nm to about 10 nm.

9. The supported, bimetallic catalyst system as in claim 1, wherein the shell metal defines a thickness on the core metal that is up to about 20 nm.

10. The supported, bimetallic catalyst system as in claim 1, wherein the shell metal defines a thickness on the core metal that is about 10 nm to about 20 nm.

11. The supported, bimetallic catalyst system as in claim 1, wherein the shell metal defines a thickness on the core metal that is about 0.5 nm to about 10 nm.

12. The supported, bimetallic catalyst system as in claim 1, wherein the core-shell particle has a total diameter of about 1 nm to about 25 nm on the surface of the support.

13. The supported, bimetallic catalyst system as in claim 1, wherein the core-shell particle has a total diameter of about 2 nm to about 15 nm on the surface of the support.

14. A method of hydrochlorination of acetylene, comprising: exposing acetylene to HCl and to the supported, bimetallic catalyst system of claim 1.

15. A method of reduction of sulfur trioxide, comprising: exposing sulfur trioxide to the supported, bimetallic catalyst system of claim 1.

16. A method of reforming a biogas comprising methane and carbon dioxide, the method comprising: exposing the biogas to the supported, bimetallic catalyst system of claim 1 such that a catalytic conversion is achieved to produce hydrogen gas and carbon monoxide.

* * * * *

UNITED STATES PATENT AND TRADEMARK OFFICE
CERTIFICATE OF CORRECTION

PATENT NO. : 10,016,751 B2
APPLICATION NO. : 14/854191
DATED : July 10, 2018
INVENTOR(S) : John Monnier, John Regalbuto and Kerry O'Connell Page 1 of 1

It is certified that error appears in the above-identified patent and that said Letters Patent is hereby corrected as shown below:

On the Title Page

Under (72) Inventors:
"John Monnier, Columbia, SC (US);
John Regalbuto, Columbia, SC (US);
Kerry O'Connell, Columbia, SC (US)"
Should read:
"John Monnier, Columbia, SC (US);
John Regalbuto, Columbia, SC (US);
Kerry O'Connell, Columbia, SC (US);
Daniel M. Ginosaur, Idaho Falls, ID (US)"

In the Specification

Under Column 1, immediately after the "PRIORITY INFORMATION" paragraph and immediately before the heading "BACKGROUND", the following header and statement need to be added:
STATEMENT AS TO RIGHTS TO INVENTIONS MADE UNDER FEDERALLY SPONSORED RESEARCH
This invention was made with government support under Contract No. DE-AC07-05-ID14517, awarded by the United States Department of Energy. The government has certain rights in the invention.

Signed and Sealed this
Twenty-third Day of January, 2024

Katherine Kelly Vidal
*Director of the United States Patent and Trademark Office*